United States Patent [19]

Klotz

[11] 4,269,813

[45] May 26, 1981

[54] CRYSTALLINE BOROSILICATE AND PROCESS OF PREPARATION

[75] Inventor: Marvin R. Klotz, Batavia, Ill.

[73] Assignee: Standard Oil Company (Indiana), Chicago, Ill.

[21] Appl. No.: 897,360

[22] Filed: Apr. 18, 1978

Related U.S. Application Data

[63] Continuation-in-part of Ser. No. 836,403, Sep. 26, 1977, abandoned, Ser. No. 819,974, Jul. 28, 1977, abandoned, and Ser. No. 733,267, Oct. 18, 1976, abandoned.

[51] Int. Cl.³ .............................................. C01B 35/10
[52] U.S. Cl. .................................. 423/277; 252/432; 423/326
[58] Field of Search ..................... 423/277, 326–330; 252/431 N, 432; 260/448.2 N

[56]       References Cited
         U.S. PATENT DOCUMENTS

| | | | |
|---|---|---|---|
| 3,328,119 | 6/1967 | Robson | 423/277 |
| 3,329,482 | 4/1967 | Young | 423/326 |
| 3,431,219 | 3/1969 | Argauer | 252/455 Z |
| 3,700,585 | 10/1972 | Chen et al. | 208/111 |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 3,941,871 | 3/1976 | Dwyer et al. | 423/326 |
| 4,029,716 | 6/1977 | Kaeding | 260/672 T |
| 4,049,573 | 9/1977 | Kaeding | 252/432 |
| 4,061,724 | 12/1977 | Grose et al. | 423/335 |
| 4,067,920 | 1/1978 | Kaeding | 260/671 M |
| 4,071,377 | 1/1978 | Schwuger et al. | 423/329 X |
| 4,078,009 | 3/1978 | Kaeding | 260/673 |
| 4,088,706 | 5/1978 | Kaeding | 260/668 R |

FOREIGN PATENT DOCUMENTS 984502  2/1965  United Kingdom ..................... 423/329

*Primary Examiner*—Edward J. Meros
*Attorney, Agent, or Firm*—James L. Wilson; William T. McClain; William H. Magidson

[57]              ABSTRACT

A new crystalline borosilicate comprises a molecular sieve material having the following composition in terms of mole ratios of oxides:

$$0.9 \pm 0.2 M_{2/n}O : B_2O_3 : YSiO_2 : ZH_2O$$

wherein M is at least one cation, n is the valence of the cation, Y is a value within the range of 4 to about 600, and Z is a value within the range of 0 to about 160, and providing a specific X-ray diffraction pattern. The borosilicate is used to catalyze various processes, such as isomerization, disproportionation, and transalkylation.

41 Claims, No Drawings

CRYSTALLINE BOROSILICATE AND PROCESS OF PREPARATION

CROSS REFERENCE TO RELATED APPLICATIONS

This application is a continuation-in-part application of applications, U.S. Ser. No. 733,267, filed on Oct. 18, 1976; U.S. Ser. No. 819,974, filed on July 28, 1977; and U.S. Ser. No. 836,403, filed on Sept. 26, 1977, each now abandoned. Each of these three co-pending applications is incorporated by reference herein and is made a part hereof, including but not limited to those portions of each which specifically appear hereinafter.

BACKGROUND OF THE INVENTION

This invention relates to novel crystalline borosilicates and to their use. More particularly, this invention relates to novel borosilicate crystalline molecular sieve materials having catalytic properties and to various hydrocarbon conversion processes using such crystalline borosilicates. Relevant patent art can be found in U.S. Patent Classes 423-326, 252-458 and 260-668.

DESCRIPTION OF THE PRIOR ART

Zeolitic materials, both natural and synthetic, have been demonstrated in the past to have catalytic capabilities for many hydrocarbon processes. Zeolitic materials, often referred to as molecular sieves, are ordered porous crystalline aluminosilicates having a definite structure with large and small cavities interconnected by channels. The cavities and channels throughout the crystalline material are generally uniform in size allowing selective separation of hydrocarbons. Consequently, these materials in many instances have come to be classified in the art as molecular sieves and are utilized, in addition to the selective adsorptive processes, for certain catalytic properties. The catalytic properties of these materials are also affected, to some extent, by the size of the molecules which are allowed selectively to penetrate the crystal structure, presumably to be contacted with active catalytic sites within the ordered structure of these materials.

Generally, the term "molecular sieve" includes a wide variety of positive-ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of positive ions, for example, alkali-metal or alkaline-earth-metal cations.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (U.S. Pat. No. 2,882,243), Zeolite X (U.S. Pat. No. 2,882,244), Zeolite Y (U.S. Pat. No. 3,130,007), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), and others.

Relevant art is the above U.S. Pat. No. 3,702,886, disclosing the crystalline aluminosilicate Zeolite ZSM-5 and the method for making the same. This patent teaches the production of a zeolite wherein aluminum or gallium oxides are present in the crystalline structure, along with silicon or germanium oxides. A specific ratio of the latter to the former are reacted to produce a class of zeolites designated ZSM-5, which is limited to crystalline alumino- or gallo-silicates or germanates and which has a specified X-ray diffraction pattern. The above ZSM-11 and ZSM-12 patents are similarly limited to crystalline alumino- or gallo-silicates or germanates, also having specified X-ray diffraction patterns.

Manufacture of the ZSM materials utilizes a mixed based system in which sodium aluminate and a silicon-containing material are mixed together with sodium hydroxide and an organic base, such as tetrapropylammonium hydroxide or tetrapropylammonium bromide, under specified reaction conditions, to form the desired crystalline aluminosilicate.

U.S. Pat. No. 3,941,871 claims and teaches an organosilicate having very little aluminum in its crystalline structure and possessing an X-ray diffraction pattern similar to the ZSM-5 composition. This patent is considered relevant art.

Another relevant patent is U.S. Pat. No. 3,328,119, which is directed to a synthetic crystalline aluminosilicate containing a minor amount of boria as an integral part of its crystal framework. This reference has been cited by the Examiner during the prosecution of co-pending applications U.S. Ser. No. 819,974 and U.S. Ser. No. 836,403.

Additional relevant art comprises U.S. Pat. Nos. 3,329,480; 3,329,481; 4,029,716; and 4,078,009. U.S. Pat. Nos. 3,329,480 and 3,329,481 relate to "zircono-silicates" and "titano-silicates", respectively. U.S. Pat. Nos. 4,029,716 and 4,078,009 relate to a crystalline aluminosilicate zeolite having a silica-to-alumina ratio of at least about 12 and a constraint index within the approximate range of 1 to 12, and having combined therewith boron in an amount of at least about 0.2 weight percent as a result of reaction of the zeolite with a boron-containing compound.

The present invention, however, relates to a novel family of stable synthetic crystalline materials characterized as borosilicates identified as AMS-1B and having a specified X-ray diffraction pattern. The claimed AMS-1B crystalline borosilicates are formed by reacting a boron oxide and a silicon-containing material in a basic medium.

SUMMARY OF THE INVENTION

Broadly, according to the present invention, there is provided a crystalline borosilicate which comprises a molecular sieve material having the following composition in terms of mole ratios of oxides:

$$0.9 \pm 0.2\ M_{2/n}O:B_2O_3:YSiO_2:ZH_2O$$

wherein M is at least one cation having a valence of n, Y is between 4 and about 600, and Z is between 0 and about 160.

Embodiments of such borosilicate provide an X-ray diffraction pattern comprising the following X-ray diffraction lines:

| d (Å) | Assigned Strength |
| --- | --- |
| 11.2 ± 0.2 | W-VS |
| 10.0 ± 0.2 | W-MS |

-continued

| d (Å) | Assigned Strength |
|---|---|
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | wherein the assigned strengths correspond to the following values of relative peak heights:

| Assigned Strength | Relative Peak Height |
|---|---|
| VW | less than 10 |
| W | 10-19 |
| M | 20-39 |
| MS | 40-70 |
| VS | greater than 70 |

A range of assigned strengths comprises all strengths between the limits shown.

Embodiments of these borosilicates are prepared by the method which comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

There is also provided a process for conversion of a hydrocarbon stream, which process comprises contacting said hydrocarbon stream at conversion conditions with a crystalline borosilicate as defined hereinabove.

In another embodiment, there is provided a process for the isomerization of a xylene-containing feed, which process comprises contacting said feed at isomerization conditions with the aforedescribed crystalline borosilicate.

Broadly, in accordance with the present invention, there is also provided a method for preparing a crystalline borosilicate which comprises a molecular sieve material having the following composition in terms of mole ratios of oxides:

$$0.9 \pm 0.2 \ M_{2/n}O:B_2O_3:YSiO_2:ZH_2O$$

wherein M is at least one cation having a valence of n, Y is between 4 and about 600, and Z is between 0 and about 160, which method comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

Examples of more specific embodiments that are provided according to the present invention are as follows:

In one embodiment, there is provided a crystalline borosilicate having a composition in terms of mole ratios of oxides as follows:

$$0.9 \pm 0.2 \ M_{2/n}O:B_2O_3:YSiO_2:ZH_2O$$

wherein M is at least one cation having a valence of n, Y is between 4 and about 500, and Z is between 0 and about 160, said borosilicate showing the X-ray diffraction lines of Table V of the specification.

In another embodiment, there is provided a crystalline borosilicate having a composition in terms of mole ratios of oxides as follows:

$$0.9 \pm 0.2 \ M_{2/n}O:B_2O_3:YSiO_2:ZH_2O$$

wherein M is at least one cation having a valence of n, Y is between 4 and about 300, and Z is between 0 and about 160, said borosilicate having the X-ray diffraction lines and assigned strength substantially as described in Table II of the specification.

In still another embodiment, there is provided a method for preparing a crystalline borosilicate possessing X-ray diffraction lines and relative intensities substantially as shown in Table IX, which method comprises preparing a mixture containing an oxide of silicon, an oxide of boron, a base of an alkali or alkaline earth metal, a tetraethylammonium cation, and water; maintaining said mixture at reaction conditions including a temperature in the range of from about 100° C. to about 250° C. to effect formation of said composition.

The crystalline borosilicate of the present invention can be employed in various processes, some of which are reforming, hydrocracking, transalkylation, disproportionation, isomerization, and alkylation. They are particularly suitable for the isomerization of xylenes and conversion of ethylbenzene and they can be used to convert alcohols, such as methanol, to useful products, such as aromatics or olefins.

DESCRIPTION AND SPECIFIC EMBODIMENTS

The present invention relates to a novel synthetic crystalline molecular sieve material, a crystalline borosilicate. The family of such crystalline borosilicate materials, which are identified as AMS-1B borosilicates, has a particular Xray diffraction pattern as is shown in the various tables hereinafter. Such crystalline borosilicate can generally be characterized, in terms of the mole ratios of oxides, as follows in Equation I:

$$0.9 \pm 0.2 \ M_{2/n}O:B_2O_3:YSiO_2:ZH_2O \quad \text{(I)}$$

wherein M is at least one cation, n is the valence of the cation, Y is between 4 and about 600, and Z representing the water present in such material is between 0 and about 160, or more.

In another instance, the claimed crystalline borosilicate can be represented in terms of mole ratios of oxides for the crystalline material not yet activated or calcined at high temperatures as follows in Equation II:

$$0.9 \pm 0.2 [WR_2O + (1-W)M_{2/n}O]:B_2O_3:YSiO_2:ZH_2O \quad \text{(II)}$$

wherein R is an alkylammonium cation, M is at least one cation, n is the valence of the cation, Y is a value between 4 and 600, Z is a value between 0 and about 160, and W is a value greater than 0 and less than 1.

In Equation I, M can represent an alkali-metal cation, an alkaline-earth-metal cation, an ammonium cation, an alkylammonium cation, a hydrogen cation, a catalytically-active-metal cation, or mixtures thereof. In Equation II, M can represent an alkali-metal cation, an alkaline-earth-metal cation, an ammonium cation, a hydrogen cation, a catalytically-active metal cation, or mixtures thereof.

Advantageously, the value for Y falls within the range of 4 to about 500. Suitably, Y is 4 to about 300; preferably, about 50 to about 160; and more preferably, about 80 to about 120.

Suitably, Z is within the range of 0 to about 40.

The original cation "M" in the above formulations can be replaced in accordance with techniques well-known in the art, at least in part by ion exchange with other cations. Preferred replacing cations include tetraalkylammonium cations, metal ions, ammonium ions, hydrogen ions, and mixtures of the above. Particularly preferred cations are those which render the AMS-1B crystalline borosilicate catalytically active, especially for hydrocarbon conversion. These materials include hydrogen, rare earth metals, aluminum, metals of Groups IB, IIB and VIII of the Periodic Table, noble metals, manganese, and other catalytically active materials and metals known to the art. The catalytically active components can be present anywhere from about 0.05 to about 25 weight percent of the AMS-1B crystalline borosilicate.

Members of the family of AMS-1B crystalline borosilicates possess a specified and distinctive crystalline structure. Two methods were employed to obtain X-ray diffraction patterns of various samples of AMS-1B crystalline borosilicates.

In the first method, identified hereinafter as Method No. 1, a Phillips instrument which utilized copper K alpha radiation was employed. The theta angles were recorded on a strip chart using a proportional counter. The theta values recorded were converted to interplanar spacing values in Angstroms (Å) using the Bragg equation. The relative intensities (relative peak heights) were calculated as $(100\ I/I_o)$, where $I_o$ is the intensity of the strongest recorded peak and I is the value actually read for the particular interplanar spacing.

In the second method, identified hereinafter as Method No. 2, the X-ray diffractometer was a Phillips instrument which utilized copper K alpha radiation in conjunction with an AMR focusing monochromometer and a theta compensating slit, in which its aperture varies with the theta angle. The output from the diffractometer was processed through a Canberra hardware/software package and reported by way of a strip chart and tabular printout. The compensating slit and the Canberra package tend to increase the peak/background ratios while reducing the peak intensities at low theta angles [large interplanar spacings] and increasing the peak intensities at high theta angles [small interplanar spacings].

For ease of reporting the results obtained by either method, the relative intensities (relative peak heights) were arbitrarily assigned the following values:

| Relative Peak Height | Assigned Strength |
| --- | --- |
| less than 10 | VW (very weak) |
| 10–19 | W (weak) |
| 20–39 | M (Medium) |
| 40–70 | MS (medium strong) |
| greater than 70 | VS (very strong) |

These assigned strengths are used throughout this application.

An X-ray diffraction pattern obtained by means of Method No. 1 and displaying the significant lines in the indicated relative intensities (relative peak heights) and assigned strengths for the AMS-1B crystalline borosilicates is presented in Table I hereinbelow:

TABLE I

| Interplanar Spacings, d(Å) | Relative Intensity $(I/I_o)$ | Assigned Strength |
| --- | --- | --- |
| 11.04 ± 0.2 | 100 | VS |
| 10.04 ± 0.2 | 68 | MS |
| 7.37 ± 0.15 | 2 | VW |
| 6.70 ± 0.1 | 7 | VW |
| 6.32 ± 0.1 | 10 | W |
| 5.98 ± 0.07 | 20 | M |
| 5.68 ± 0.07 | 10 | W |
| 5.53 ± 0.05 | 13 | W |
| 5.30 ± 0.05 | 3 | VW |
| 5.21 ± 0.05 | 3 | VW |
| 4.98 ± 0.05 | 9 | VW |
| 4.62 ± 0.05 | 3 | VW |
| 4.37 ± 0.05 | 5 | VW |
| 4.27 ± 0.05 | 10 | W |
| 4.07 ± 0.05 | 2 | VW |
| 4.00 ± 0.05 | 6 | VW |
| 3.83 ± 0.05 | 84 | VS |
| 3.72 ± 0.05 | 48 | MS |
| 3.64 ± 0.05 | 23 | M |
| 3.42 ± 0.05 | 9 | VW |
| 3.30 ± 0.05 | 11 | W |
| 3.23 ± 0.05 | 3 | VW |
| 3.16 ± 0.05 | 2 | VW |
| 3.12 ± 0.05 | 2 | VW |
| 3.04 ± 0.05 | 9 | VW |
| 2.98 ± 0.02 | 16 | W |
| 2.94 ± 0.02 | 10 | W |
| 2.86 ± 0.02 | 2 | VW |
| 2.83 ± 0.02 | 1 | VW |
| 2.73 ± 0.02 | 3 | VW |
| 2.59 ± 0.02 | 3 | VW |
| 2.55 ± 0.02 | 3 | VW |
| 2.51 ± 0.02 | 3 | VW |
| 2.48 ± 0.02 | 5 | VW |
| 2.45 ± 0.02 | 3 | VW |
| 2.39 ± 0.02 | 5 | VW |
| 2.00 ± 0.02 | 13 | W |
| 1.99 ± 0.02 | 14 | W |
| 1.94 ± 0.02 | 6 | VW |
| 1.91 ± 0.02 | 4 | VW |
| 1.86 ± 0.02 | 2 | VW |
| 1.81 ± 0.02 | 1 | VW |
| 1.75 ± 0.02 | 2 | VW |
| 1.66 ± 0.02 | 4 | VW |
| 1.56 ± 0.02 | 2 | VW |

When Method No. 1 is employed, the above X-ray pattern is characteristic of the AMS-1B crystalline borosilicate having the oxide mole formula described in Equation I, which borosilicate has been calcined at 1100° F. (593° C.) and wherein the tetraalkylammonium ion has been removed from the system by the calcination procedure.

In the following Table, the more significant interplanar spacings and their assigned strength are summarized from Table I.

TABLE II

| Interplanar Spacings, d(Å) | Assigned Strengths |
| --- | --- |
| 11.04 ± 0.2 | VS |

TABLE II-continued

| Interplanar Spacings, d(Å) | Assigned Strengths |
|---|---|
| 10.04 ± 0.2 | MS |
| 5.98 ± 0.07 | M |
| 3.83 ± 0.05 | VS |
| 3.72 ± 0.05 | MS |
| 3.64 ± 0.05 | M |

In instances in which the AMS-1B crystalline borosilicate in an as-produced state (prior to high temperature calcination, but after some reasonable amount of drying has taken place), is analyzed by X-ray diffraction analysis by Method No. 1, the crystalline borosilicate generally is characterized by Equation II above and has an X-ray diffraction pattern showing the following significant lines:

TABLE III

| Interplanar Spacing, d(Å) | Assigned Strength |
|---|---|
| 11.04 ± 0.2 | MS |
| 9.82 ± 0.2 | MS |
| 9.60 ± 0.2 | MW |
| 8.84 ± 0.2 | VW |
| 7.37 ± 0.2 | W |
| 7.02 ± 0.15 | VW |
| 6.60 ± 0.1 | VW |
| 6.32 ± 0.1 | W |
| 5.90 ± 0.07 | W |
| 5.68 ± 0.07 | W |
| 5.53 ± 0.05 | W |
| 5.27 ± 0.05 | VW |
| 5.09 ± 0.05 | VW |
| 4.95 ± 0.05 | W |
| 4.57 ± 0.05 | W |
| 4.44 ± 0.05 | VW |
| 4.35 ± 0.05 | W |
| 4.23 ± 0.05 | W |
| 4.04 ± 0.05 | VW |
| 3.97 ± 0.05 | W |
| 3.80 ± 0.05 | VS |
| 3.72 ± 0.05 | M |
| 3.67 ± 0.05 | MS |
| 3.60 ± 0.05 | MS |
| 3.45 ± 0.05 | VW |
| 3.41 ± 0.05 | W |
| 3.30 ± 0.05 | W |
| 3.28 ± 0.05 | W |
| 3.23 ± 0.05 | VW |
| 3.16 ± 0.05 | VW |
| 3.12 ± 0.05 | VW |
| 3.06 ± 0.05 | W |
| 2.96 ± 0.02 | W |
| 2.94 ± 0.02 | W |
| 2.85 ± 0.02 | VW |
| 2.76 ± 0.02 | VW |
| 2.71 ± 0.02 | W |
| 2.59 ± 0.02 | W |
| 2.56 ± 0.02 | VW |
| 2.49 ± 0.02 | VW |
| 2.47 ± 0.02 | W |
| 2.40 ± 0.02 | VW |
| 2.38 ± 0.02 | W |
| 2.33 ± 0.02 | VW |
| 2.31 ± 0.02 | VW |
| 2.28 ± 0.02 | VW |
| 2.21 ± 0.02 | VW |
| 2.19 ± 0.02 | VW |
| 2.16 ± 0.02 | VW |
| 2.10 ± 0.02 | VW |
| 2.06 ± 0.02 | VW |
| 2.00 ± 0.02 | W |
| 1.99 ± 0.02 | W |
| 1.94 ± 0.02 | W |
| 1.90 ± 0.02 | W |
| 1.86 ± 0.02 | W |
| 1.82 ± 0.02 | VW |
| 1.75 ± 0.02 | W |
| 1.71 ± 0.02 | VW |

TABLE III-continued

| Interplanar Spacing, d(Å) | Assigned Strength |
|---|---|
| 1.66 ± 0.02 | W |

In the following Table, the more significant interplanar spacings and their assigned strengths are summarized from Table III.

TABLE IV

| Interplanar Spacing, d(Å) | Assigned Strength |
|---|---|
| 11.04 ± 0.2 | MS |
| 9.82 ± 0.2 | MS |
| 3.80 ± 0.05 | VS |
| 3.72 ± 0.05 | M |
| 3.67 ± 0.05 | MS |
| 3.60 ± 0.05 | MS |

A typical X-ray diffraction pattern obtained by means of Method No. 2 and displaying the significant lines which have relative intensities (relative peak heights) of 11 or higher for an AMS-1B crystalline borosilicate after calcination at 1000° F. (538° C.) is shown in Table V hereinbelow.

TABLE V

| Interplanar Spacing, d(Å) | Relative Intensity | Assigned Strength |
|---|---|---|
| 11.3 ± 0.2 | 38 | M |
| 10.1 ± 0.2 | 30 | M |
| 6.01 ± 0.07 | 14 | W |
| 4.35 ± 0.05 | 11 | W |
| 4.26 ± 0.05 | 14 | W |
| 3.84 ± 0.05 | 100 | VS |
| 3.72 ± 0.05 | 52 | MS |
| 3.65 ± 0.05 | 31 | M |
| 3.44 ± 0.05 | 14 | W |
| 3.33 ± 0.05 | 16 | W |
| 3.04 ± 0.05 | 16 | W |
| 2.97 ± 0.02 | 22 | M |
| 2.48 ± 0.02 | 11 | W |
| 1.99 ± 0.02 | 20 | M |
| 1.66 ± 0.02 | 12 | W |

An AMS-1B borosilicate which has been only subjected to mild drying at 165° C. (as-produced material) possesses an X-ray diffraction pattern obtained by Method No. 2, which pattern has the following significant lines:

TABLE VI

| Interplanar Spacing, d(Å) | Relative Intensity | Assigned Strength |
|---|---|---|
| 11.4 ± 0.2 | 19 | W |
| 10.1 ± 0.2 | 17 | W |
| 3.84 ± 0.05 | 100 | VS |
| 3.73 ± 0.05 | 43 | MS |
| 3.66 ± 0.05 | 26 | M |
| 3.45 ± 0.05 | 11 | W |
| 3.32 ± 0.05 | 13 | W |
| 3.05 ± 0.05 | 12 | W |
| 2.98 ± 0.02 | 16 | W |
| 1.99 ± 0.02 | 10 | W |
| 1.66 ± 0.02 | 20 | M |

The strip chart recordings of the calcined borosilicate reported in Table V above showed that this material had the following X-ray diffraction lines:

TABLE VII

| Interplanar Spacing, d(Å) | |
|---|---|
| Run 1 | Run 2* |
| 11.3 | 11.2 |

TABLE VII-continued

| Interplanar Spacing, d(Å) | |
|---|---|
| Run 1 | Run 2* |
| 10.2 | 10.0 |
| 7.49 | 7.37 |
| 6.70 | 6.70 |
| 6.41 | 6.36 |
| 6.02 | 5.98 |
| 5.71 | 5.67 |
| 5.60 | 5.57 |
| 5.01 | 5.34 |
| 4.62 | 5.01 |
| 4.37 | 4.62 |
| 4.27 | 4.35 |
| 4.00 | 4.25 |
| 3.85 | 4.00 |
| 3.72 | 3.85 |
| 3.64 | 3.70 |
| 3.48 | 3.64 |
| 3.44 | 3.46 |
| 3.30 | 3.42 |
| 3.14 | 3.30 |
| 3.04 | 3.25 |
| 2.98 | 3.12 |
| 2.86 | 3.04 |
| 2.71 | 2.97 |
| 2.60 | 2.86 |
| 2.48 | 2.71 |
| 2.39 | |
| 2.32 | |
| 2.22 | |
| 2.00 | |
| 1.99 | |
| 1.95 | |
| 1.91 | |
| 1.86 | |
| 1.75 | |
| 1.66 | |

*This run terminated at 2.71 d(Å)

The AMS-1B crystalline borosilicates of the present invention are useful as catalysts for various hydrocarbon conversion processes and they are suitable for chemical adsorption. Some of the hydrocarbon conversion processes for which the borosilicates appear to have relatively useful catalytic properties are fluidized catalytic cracking; hydrocracking; the isomerization of normal paraffins and naphthenes; the reforming of naphthas and gasoline-boiling-range feedstocks; the isomerization of aromatics, especially the isomerization of alkylaromatics, such as xylenes; the disproportionation of aromatics, such as toluene, to form mixtures of other more valuable products including benzene, xylene, and other higher methyl substituted benzenes; hydrotreating; alkylation; hydrodealkylation; hydrodesulfurization; and hydrodenitrogenation. They are particularly suitable for the isomerization of alkylaromatics, such as xylenes, and for the conversion of ethylbenzene. The AMS-1B borosilicates, in certain ion-exchanged forms, can be used to convert alcohols, such as methanol, to useful products, such as aromatics or olefins.

When the AMS-1B crystalline borosilicate is used as a hydrocracking catalyst, hydrocracking charge stocks can pass over the catalyst at temperatures anywhere from about 500° F. to about 850° F. (about 260° C. to about 454° C.) or higher using known molar ratios of hydrocarbon to hydrogen and varying pressures anywhere from a few up to many thousands of pounds per square inch or higher. The weight hourly space velocity and other process parameters can be varied consistent with the well-known teachings of the art.

The specified AMS-1B crystalline borosilicate is also suitable as a reforming catalyst to be used with the appropriate hydrogenation components at well-known reforming conditions including temperatures of anywhere from about 500° F. to 1050° F. (about 260° C. to about 566° C.), or more, pressures anywhere from a few up to 300 psig to 1000 psig, and weight hourly space velocities and hydrogen-to-hydrocarbon mole ratios consistent with those well known in the reforming art.

The present composition is also suitable for hydrocarbon isomerization and disproportionation. It is especially useful for liquid or vapor phase isomerization of xylenes and especially the isomerization of mixed xylenes to predominantly paraxylene products. Operating conditions for the isomerization of a xylene feed broadly comprise a temperature of about 200° F. to about 1000° F. (about 93° C. to about 538° C.), a hydrogen-to-hydrocarbon mole ratio of about 0 to about 20, a weight hourly space velocity (WHSV) of about 0.01 weight unit of feed per hour per weight unit of catalyst ($hr^{-1}$) to about 90 $hr^{-1}$, and a pressure of about 0 psig to about 1000 psig. Advantageously, the conditions comprise a temperature of about 400° F. to about 900° F. (about 204° C. to about 482° C.), a hydrogen-to-hydrocarbon mole ratio of about 1 to about 12, and a WHSV of about 1 $hr.^{-1}$ to about 20 $hr.^{-1}$, and a pressure of about 10 psig to about 500 psig. The preferred conditions for the isomerization of xylenes comprise a temperature of about 600° F. to about 850° F. (about 316° C. to about 454° C.), a hydrogen-to-hydrocarbon mole ratio of about 2 to about 8, a WHSV of about 1 $hr.^{-1}$ to about 10 $hr.^{-1}$, and a pressure of about 100 psig to about 300 psig. The choice of catalytically active metals to be placed on the AMS-1B crystalline borosilicate can be selected from any of those well known in the art. Nickel seems to be especially appropriate for isomerization of aromatics. When used as a catalyst in isomerization processes with suitable cations placed on the ion-exchangeable sites within the AMS-1B crystalline borosilicate, reasonably high selectivities for production of desired isomers are obtained.

The claimed AMS-1B crystalline borosilicates can also be used as adsorbents to selectively adsorb specific isomers or hydrocarbons in general from a liquid or vapor stream.

The ability of these materials to be stable under high temperatures or in the presence of other normal deactivating agents appears to make this class of crystalline materials relatively valuable for high-temperature operations including the cyclical types of fluidized catalytic cracking or other processing.

The AMS-1B crystalline borosilicates can be used as catalysts or as adsorbents whether in the alkali-metal or alkaline-earth-metal forms, the ammonium form, the hydrogen form, or any other univalent or multivalent cationic form. Mixtures of cations may be employed. The AMS-1B crystalline borosilicates can also be used in intimate combination with a hydrogenating component, such as tungsten, vanadium, molybdenum, rhenium, nickel, cobalt, chromium, manganese, or a noble metal, such as platinum or palladium, or rare earth metals, where a hydrogenation-dehydrogenation function is to be performed. Such components can be exchanged into the composition at the cationic sites, represented by the term "M" in the above formulae, impregnated therein or physically intimately admixed therewith. In one example, platinum can be placed on the borosilicate with a platinum-metal-containing ion.

The impregnation of a hydrogenation metal on the borosilicate or on a support comprising the crystalline borosilicate suspended in and distributed throughout a matrix of a porous refractory inorganic oxide, such as an alumina, often results in a suitable catalytic composition. For example, a catalyst comprising molybdenum impregnated on a composition of AMS-1B crystalline borosilicate suspended in an alumina matrix, when used to isomerize a feed of mixed xylenes, furnishes better selectivity and higher by-product values.

The original cation associated with the AMS-1B crystalline borosilicate can be replaced, as mentioned above, by a wide variety of other cations according to techniques which are known in the art. Ion exchange techniques known in the art are disclosed in many patents including U.S. Pat. Nos. 3,140,249, 3,140,251, and 3,140,253, the teachings of which are incorporated by reference into this specification.

A catalytically active material can be placed onto the borosilicate structure by ion exchange, impregnation, or other suitable contact means, followed by washing, drying at about 150° F. to 600° F. (about 66° C. to about 316° C.), and then calcining in a suitable atmosphere, such as air, nitrogen, or combinations thereof, at about 500° F. to about 1500° F. (about 260° C. to about 816° C.), typically about 1000° F. (about 520° C.), usually for about 0.5 hour to about 20 hours. This procedure can be repeated one or more times. Advantageously, before placing a catalytically active metal ion on the borosilicate structure, the borosilicate is in the hydrogen form which, typically, is produced by exchange with ammonium ion followed by calcination.

Ion-exchange within the cationic site within the crystalline material will generally have a relatively insignificant effect on the overall X-ray diffraction pattern that the crystalline borosilicate material generates. Small variations may occur at various spacings on the X-ray pattern, but the overall pattern remains essentially the same. Small changes in the X-ray diffraction patterns may also be the result of processing differences during manufacture of the borosilicate; however, the material will still fall within the generic class of AMS-1B crystalline borosilicates defined in terms of their X-ray diffraction patterns as shown in the tables found herein, or in the examples that follow.

The crystalline borosilicate of the present invention may be incorporated as a pure borosilicate in a catalyst or adsorbent or may be admixed with various binders or bases depending upon the intended process use. In many instances, the crystalline borosilicate can be pelletized or extruded. The crystalline borosilicate can be combined with active or inactive materials, synthetic or naturally-occurring zeolites, as well as inorganic or organic materials which would be useful for binding the borosilicate. Other well-known materials include mixtures of silica, silica-alumina, alumina sols, clays, such as bentonite or kaolin, or other binders well known in the art. The crystalline borosilicate can also be mixed intimately with porous matrix materials, such as silica-zirconia, silica-magnesia, silica-alumina, silica-thoria, silica-beryllia, silica-titania, as well as three component compositions including, but not limited to, silica-alumina-thoria and many other materials well known in the art. The crystalline borosilicate content can vary anywhere from a few up to 100 wt.% of the total finished product. Typical catalytic compositions contain about 5 wt.% to about 80 wt.% borosilicate material.

The AMS-1B crystalline borosilicate generally can be prepared by mixing an aqueous medium of oxides of boron, an alkali metal or an alkaline earth metal, such as sodium, and silicon, together with alkylammonium cations or a precursor of alkylammonium cations, such as an alkylamine, an alkylamine plus an alkyl hydroxide, an alkylamine plus an alkyl halide, or an alkylamine plus an alkyl acetate. The alkyl groups in the alkylammonium cations may be the same, or mixed, such as tetraethyl-, or diethyl-dipropyl-ammonium cations. The mole ratios of the various reactants can be varied considerably to produce the AMS-1B crystalline borosilicates. In particular, the mole ratios of the initial reactant concentrations for producing the borosilicate can vary as is indicated in Table VIII below.

Examples of oxides of boron are $H_3BO_3$, $B_2O_3$, and $B_4O_7$. Examples of oxides of silicon are silicic acid, sodium silicate, tetraalkyl silicates, and Ludox, which is a stabilized polymer of silicic acid manufactured by E. I. du Pont de Nemours & Co. Suitable compounds of the alkali metals or alkaline earth metals are their hydroxides.

TABLE VIII

| | Broad | Preferred | Most Preferred |
|---|---|---|---|
| $SiO_2/B_2O_3$ | 5–400 | 10–150 | 10–80 |
| $R_2O+/(R_2O+ + M_{2/n}O)$ | 0.1–1 | 0.2–0.97 | 0.3–0.97 |
| $OH^-/SiO_2$ | 0.01–11 | 0.1–2 | 0.1–1 |
| $H_2O/OH$ | 10–4000 | 10–500 | 10–500 | where R is an alkylamine or alkylammonium cation, preferably tetra-n-propyl ammonium cation or tetraethyl ammonium cation, and M is at least one cation having the valence of n, such as an alkali-metal or an alkaline-earth-metal cation. The above quantities can be varied in concentration in the aqueous medium.

During preparation, acidic conditions generally should be avoided. Although when ammonium hydroxide is used as a base, borosilicates can be produced with initial pH's of 5.8, or lower. When alkali metal hydroxides are used, the values of the ratio of $OH^-/SiO_2$ in Table VIII should furnish a pH of the system that broadly falls within the range of about 9 to about 13.5. Advantageously, the pH of the reaction system falls within the range of about 10.5 to about 11.5. Preferably, the pH of the system is about 10.8 to about 11.2. A proper pH is conducive to the incorporation of boron into the molecular sieve structure.

By simple regulation of the quantity of boron (represented as $B_2O_3$) in the reaction mixture, it is possible to vary the $SiO_2/B_2O_3$ molar ratio in the final product in a range of from about 40 to about 600, or more. In instances where an effort is made to minimize aluminum in the borosilicate crystal structure, the molar ratios of $SiO_2/Al_2O_3$ can easily exceed a ratio of 2000:1–3000:1 or more. This ratio is generally only limited by the availability of aluminum-free raw materials.

Molar ratios of $SiO_2/B_2O_3$ in the final crystalline product can vary from 4 to about 600, or more. Actual laboratory preparations under the general conditions described herein produce $SiO_2/B_2O_3$ molar ratios starting around 60 or lower. Lower ratios might be produced using production methods which still are in the scope of the teachings of this specification.

Based on known properties of mordenite and ferrierite aluminosilicates, the present crystalline borosilicates will have about 4.5 $BO_4$ tetrahydra per unit cell at Si- $O_2/B_2O_3$ molar ratios around 80. In view of this, it would appear that single $BO_4$ exists at $SiO_2/B_2O_3$ ratios around 400. Substantially above this ratio there would be many unit cells which did not contain a $BO_4$ tetrahedron and the resulting crystalline structure might not be considered a borosilicate. There are no established criteria for establishing at what $SiO_2/B_2O_3$ molar ratio the crystalline material ceases to be a borosilicate. It seems safe to assume that at high $SiO_2/B_2O_3$ values (above about 600), the influence of the $BO_4$ tetrahedra in the crystalline structure becomes somewhat diminished and the crystalline material no longer would be referred to as a borosilicate.

Unit cell measurements of the AMS-1B crystalline borosilicates showed a linear decrease of the unit cell size with respect to an increasing boron concentration in the molecular sieve over a $SiO_2$-$B_2O_3$ range of about 80 to about 600. Ion-exchange in the AMS-1B borosilicate has shown also that there is one equivalent of alkali metal or alkaline earth metal per mole of boron, as required for electrovalent neutrality.

Under reasonably controlled conditions using the above information the claimed AMS-1B crystalline borosilicate will be produced. Typical reaction conditions include heating the reactants to a temperature of anywhere from about 25° C. to about 300° C. (about 77° F. to about 572° F.), or higher, for a period of time of anywhere from about one hour to four weeks, or more. Preferred temperature ranges are anywhere from about 90° C. to about 250° C. (about 194° F. to about 482° F.) with an amount of time necessary for the precipitation of the AMS-1B crystalline borosilicate. A preferred reaction time varies from about 4 hours to about 2 weeks. A more preferred temperature varies from about 100° C. to about 250° C. (about 212° F. to about 482° F.) and a more preferred reaction time varies from about 6 hours to about 1 week. Especially preferred conditions include a temperature around 165° C. (329° F.) for a period of about 5 days.

The material thus formed can be separated and recovered by well-known means, such as filtration. This material can be mildly dried for anywhere from a few hours to a few days at varying temperatures to form a dry cake which itself can then be crushed to a powder or to small particles and extruded, pelletized, or made into forms suitable for its intended use. Typically, the material prepared after the mild drying conditions will contain the alkylammonium ion within the solid mass and a subsequent activation or calcination procedure is necessary, if it is desired to remove this material from the formed product.

Typically, the high-temperature calcination will take place at temperatures anywhere from about 500° F. to about 1600° F. (about 260° C. to about 871° C.), or higher. Extreme calcination temperatures may prove detrimental to the crystal structure or may totally destroy it. There is generally no need for going beyond about 1100° F. (about 593° C.) in order to remove the alkylammonium cation from the original crystalline material formed.

In a typical preparation of an AMS-1B crystalline borosilicate, a compound of an alkali metal or an alkaline earth metal, such as sodium hydroxide, and a compound of boron, such as boric acid, are dissolved in water (preferably, distilled or deionized water). A tetraalkylammonium compound, such as tetra-n-propylammonium bromide, is added to the above solution and the pH of the resulting solution is adjusted to a value of about $11.0 \pm 0.2$ by the addition of base or acid. A compound of silicon, such as silica, is added rapidly to the solution, while the solution is being agitated vigorously. Vigorous agitation is continued for about 15 minutes. After the pH of the resulting solution is adjusted to about $11.0 \pm 0.2$, it is placed in an autoclave that is maintained at a temperature of about 165° C. Preferably, a stirred autoclave is used. The solution is kept in the autoclave for about 5 days for crystallization. It is preferred that the crystallization temperature be maintained below the decomposition temperature of the tetraalkylammonium compound. At the completion of the crystallization, the crystalline molecular sieve is removed from the autoclave, filtered, and washed with water. The molecular sieve material is dried in a forced draft oven at 110° C. for about 16 hours and is then heated in air in a manner such that the temperature rise does not exceed 125° C. per hour until a temperature of about 1000° F. (about 538° C.) is reached. Calcination at this temperature is then continued for about 4 hours.

Typically, the surface area of the resulting molecular sieve, as determined by BET surface area analysis, is about 350 m$^2$/gm to about 390 m$^2$/gm and the sieve particles have a maximum diameter, as determined by a scanning electron microscope, of about 2 microns.

Typically, an active hydrocarbon conversion catalyst is prepared by ion-exchanging a borosilicate, as prepared above, one or more times with an aqueous solution of ammonium acetate at a temperature of about 85° C. to 100° C. and drying, as described above, the ion-exchanged molecular sieve. The borosilicate is converted to the hydrogen form. Then the metallic cations, for example, nickel ions, are introduced onto the borosilicate, typically, by exchanging the sieve several times with an aqueous solution of a compound of the metal, for example, nickelous nitrate, at a temperature of about 85° C. to about 100° C.

Then the catalyst composition is formed by dispersing the finely-divided metal-exchanged borosilicate in a sol or gel of a high-grade-purity gamma-alumina and adding, while stirring, a solution of ammonium hydroxide to promote gelation. The resulting mixture is dried and calcined, as described above, pulverized to a convenient particle size, and formed into pellets or extrudate.

Another typical powder X-ray diffraction pattern of the AMS-1B borosilicate, which pattern was obtained by means of Method No. 1 after the crystalline borosilicate had been calcined at 1100° F., displays the significant lines in the indicated relative intensities (relative peak heights) and assigned strengths presented in Table IX hereinbelow:

TABLE IX

| Interplanar Spacings, d(Å) | Relative Intensity ($I/I_0$) | Assigned Strength |
|---|---|---|
| 11.04 ± 0.2 | 48 | MS |
| 10.04 ± 0.2 | 34 | M |
| 6.37 ± 0.1 | 12 | W |
| 5.98 ± 0.07 | 14 | W |
| 5.68 ± 0.07 | 11 | W |
| 5.57 ± 0.05 | 14 | W |
| 4.37 ± 0.05 | 12 | W |
| 4.27 ± 0.05 | 16 | W |
| 4.07 ± 0.05 | 13 | W |
| 4.00 ± 0.05 | 10 | W |
| 3.83 ± 0.05 | 100 | VS |
| 3.72 ± 0.05 | 46 | MS |
| 3.64 ± 0.05 | 30 | M |
| 3.54 ± 0.05 | 23 | M |
| 3.42 ± 0.05 | 15 | W |
| 3.34 ± 0.05 | 12 | W |

TABLE IX-continued

| Interplanar Spacings, d(Å) | Relative Intensity (I/I₀) | Assigned Strength |
|---|---|---|
| 3.30 ± 0.05 | 15 | W |
| 3.04 ± 0.05 | 16 | W |
| 2.98 ± 0.02 | 19 | W |
| 2.48 ± 0.02 | 13 | W |

The above X-ray pattern is characteristic of the crystalline borosilicate having the oxide mole formula described in Equation I, after the borosilicate has been calcined at 1100° F. and the alkylammonium (tetraalkylammonium) cation has been removed from the system by the calcination procedure.

If the crystalline borosilicate of the present invention is analyzed for an X-ray diffraction pattern when the borosilicate is in an "as-produced state" (prior to high-temperature calcination, but after some reasonable amount of drying has taken place), the X-ray diffraction pattern resulting generally is similar to that above except the relative intensities (relative peak heights) may shift locations somewhat.

Broadly, in accordance with the present invention and in view of the above, there is provided a crystalline borosilicate which comprises a molecular sieve material having the following composition in terms of mole ratios of oxides:

$$0.9 \pm 0.2 \, M_{2/n}O:B_2O_3:YSiO_2:ZH_2O$$

wherein M is at least one cation having a valence of n, Y is between 4 and about 600, and Z is between 0 and about 160, and providing an X-ray diffraction pattern comprising the following lines:

| Interplanar Spacings, d(Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

This material is prepared by the method which comprises: (1) preparing acontaining an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

Furthermore, there is provided a process for the conversion of a hydrocarbon stream, which process comprises contacting said stream at conversion conditions with a catalyst comprising the aforesaid crystalline borosilicate.

There is also provided a process for the catalytic isomerization of a xylene feed, which process comprises contacting said feed at isomerization conditions with a catalyst comprising the aforesaid crystalline borosilicate.

In one embodiment of the present invention, there is provided a crystalline borosilicate having a composition in terms of mole ratios of oxides as follows:

$$0.9 \pm 0.2 \, M_{2/n}O:B_2O_3:YSiO_2:ZH_2O$$

wherein M is at least one cation having a valence of n, Y is between 4 and about 500, and Z is between 0 and about 160, said borosilicate showing the X-ray diffraction lines of Table V hereinabove.

In another embodiment of the present invention, there is provided a crystalline borosilicate having a composition in terms of mole ratios of oxides as follows:

$$0.9 \pm 0.2 \, M_{2/n}O:B_2O_3:YSiO_2:ZH_2O$$

wherein M is at least one cation having a valence of n, Y is between 4 and about 500, and Z is between 0 and about 160, said borosilicate showing the X-ray diffraction lines and assigned strengths substantially as described in Table V hereinabove.

In another embodiment, there is provided a crystalline borosilicate having a composition in terms of mole ratios of oxides as follows:

$$0.9 \pm 0.2 \, M_{2/n}O:B_2O_3:YSiO_2:ZH_2O$$

wherein M is at least one cation having a valence of n, Y is between 4 and about 300, and Z is between 0 and about 160, said borosilicate having the X-ray diffraction lines and assigned strengths substantially as described in Table II hereinabove.

In addition, there is provided a crystalline borosilicate having a composition in terms of oxides as follows:

$$0.9 \pm 0.2 \, (WR_2O + (1-W)M_{2/n}O):B_2O_3:YSiO_2:ZH_2O$$

wherein R is tetrapropylammonium cation, M is an alkali metal cation, W is greater than 0 and less than or equal to 1, Y is between about 4 and about 500, Z is between 0 and about 160, said borosilicate showing the X-ray diffraction lines and assigned strengths substantially as described in Table VI hereinabove.

There is provided in another embodiment of the present invention a crystalline borosilicate having a composition in terms of oxides as follows:

$$0.9 \pm 0.2 \, (WR_2O + (1-W)M_{2/n}O):B_2O_3:YSiO_2:ZH_2O$$

wherein R is tetrapropylammonium cation, M is an alkali metal cation, W is greater than 0 and less than or equal to 1, Y is between about 4 and about 300, Z is between 0 and about 160, said borosilicate having the X-ray diffraction lines and assigned strengths substantially as described in Table IV hereinabove.

Broadly, according to the present invention, there is provided a process for conversion of a hydrocarbon, which process comprises contacting said hydrocarbon at conversion conditions with a crystalline borosilicate having a composition in terms of mole ratios of oxides are as follows:

$$0.9 \pm 0.2 M_{2/n}O:B_2O_3:YSiO_2:ZH_2O$$

wherein M is at least one cation having a valence of n, Y is in the range of from about 4 to about 500, and Z is in the range of from 0 to about 160, said borosilicate showing the X-ray diffraction lines and assigned strengths as described in Table V of the specification.

Moreover, there is provided a process for catalytic isomerization of a xylene feed, which process comprises contacting said feed at isomerization conditions with a crystalline borosilicate having a composition in terms of mole ratios of oxides as follows:

$$0.9\pm0.2M_{2/n}O:B_2O_3:YSiO_2:ZH_2O$$

wherein M is at least one cation having a valence of n, Y is in the range of from about 5 to about 500, and Z is in the range of from 0 to about 160, said crystalline borosilicate showing X-ray diffraction lines and assigned strengths as described in Table V of the specification.

There is also provided a process for conversion of a hydrocarbon, which process comprises contacting said hydrocarbon at conversion conditions with a crystalline borosilicate having a composition in terms of mole ratios of oxides as follows:

$$0.9\pm0.2M_{2/n}O:B_2O_3:YSiO_2:ZH_2O$$

wherein M is at least one cation having a valence of n, Y is in the range of from about 4 to about 300, and Z is in the range of from 0 to about 160, said borosilicate having the X-ray diffraction lines and assigned strengths substantially as described in Table II of the specification.

Furthermore, there is provided a process for catalytic isomerization of a xylene feed, which process comprises contacting said feed at isomerization conditions with a crystalline borosilicate having a composition in terms of mole ratios of oxides as follows:

$$0.9\pm0.2M_{2/n}O:B_2O_3:YSiO_2:ZH_2O$$

wherein M is at least one cation having a valence of n, Y is in the range of from about 4 to about 300, and Z is in the range of from 0 to about 160, said crystalline borosilicate showing the X-ray diffraction lines and assigned strengths substantially as described in Table II of the specification.

In addition, there is also provided a method for preparing a crystalline borosilicate possessing X-ray diffraction lines and relative intensities substantially as shown in Table IX hereinabove, which method comprises: (1) preparing a mixture containing an oxide of silicon, an oxide of boron, a base of an alkali or alkaline earth metal, a tetraethylammonium cation, and water; and (2) maintaining said mixture at reaction conditions including a temperature in the range of from about 100° C. to about 250° C. to effect formation of said composition.

In another embodiment of the method for preparing a crystalline borosilicate having an X-ray diffraction pattern substantially as shown in Table IX, the method comprises: (1) preparing a mixture containing a tetraethylammonium cation, an alkali or alkaline earth base, an oxide of silicon, an oxide of boron, and water and having the ratios of the initial reactant concentrations in the following ranges:

OH⁻/SiO₂: 0.01–11
R₂O/(R₂O+M₂/ₙO): 0.2–0.97
H₂O/OH⁻: 10–4000
SiO₂/B₂O₃: 5–400 wherein R is a tetra-n-propylammonium cation or a tetraethylammonium cation, M is an alkali metal or alkaline earth metal and n is the valence of M, and (2) maintaining the reaction composition under reaction conditions including a temperature in the range of from about 100° C. to about 250° C. to effect formation of said borosilicate.

There is also provided an embodiment of the method for preparing crystalline borosilicate possessing the X-ray diffraction lines and relative intensities generally as shown in Table V, wherein the method comprise: (1) preparing a mixture containing an oxide of silicon, an oxide of boron, a base of an alkali metal or alkaline earth metal, a tetraethylammonium cation, and water; and (2) maintaining said mixture at reaction conditions including a temperature in the range of from about 100° C. to about 250° C. to effect formation of said composition.

In yet another embodiment of the method for preparing crystalline borosilicates, there is provided a method for preparing a crystalline borosilicate possessing the X-ray diffraction lines and relative intensities generally as shown in Table VI, which method comprises: (1) preparing a mixture containing an oxide of silicon, an oxide of boron, a base of an alkali metal or alkaline earth metal, a tetraethylammonium cation, and water; and (2) maintaining said mixture at reaction conditions including a temperature in the range of from about 100° C. to about 250° C. to effect formation of said composition.

There is also provided a catalytic composition which comprises a crystalline borosilicate and a porous refractory inorganic oxide, said borosilicate comprising a molecular sieve material having the following composition in terms of mole ratios of oxides:

$$0.9\pm0.2M_{2/n}O:B_2O_3:YSiO_2:ZH_2O$$

wherein M is at least one cation having a valence of n, Y is between 4 and about 600, and Z is between 0 and about 160, and providing an X-ray diffraction pattern comprising the following X-ray diffraction lines and assigned strengths:

| d(Å) | Assigned Strength |
|---|---|
| 11.2 ± 0.2 | W - VS |
| 10.0 ± 0.2 | W - MS |
| 5.97 ± 0.07 | W - M |
| 3.82 ± 0.05 | VS |
| 3.70 ± 0.05 | MS |
| 3.62 ± 0.05 | M - MS |
| 2.97 ± 0.02 | W - M |
| 1.99 ± 0.02 | VW - M | said borosilicate and said inorganic oxide having been intimately admixed with one another after said borosilicate has been calcined.

In addition, there is provided a process for the conversion of a hydrocarbon stream, which process comprises contacting said stream at conversion conditions with a catalytic composition which comprises the aforesaid crystalline borosilicate and a porous refractory inorganic oxide, said borosilicate and said inorganic oxide having been intimately admixed with one another after said borosilicate has been calcined.

Moreover, there is provided a process for the catalytic isomerization of a xylene feed, which process comprises contacting said feed at isomerization conditions with a catalytic composition which comprises the aforesaid crystalline borosilicate and a porous refractory inorganic oxide, said borosilicate and said inorganic oxide having been intimately admixed with one another after said borosilicate has been calcined.

The following examples are presented as specific embodiments of the present invention and should not be read to unduly limit or restrict the scope of the appended claims.

EXAMPLE I

The AMS-1B crystalline borosilicate was prepared by dissolving 0.25 gm of $H_3BO_3$ and 1.6 gm of NaOH in 60 gm of distilled $H_2O$. Then 9.4 gms of tetra-n-propylammonium bromide (TPAB) were added and again dissolved. Finally, 12.7 gm of Ludox AS-30 (30% solids) were added with vigorous stirring. The addition of Ludox gave a curdy, gelatinous, milky solution. This solution was placed in a crystallization vessel and sealed. The vessel was placed in a 165° C. oven and left there for 7 days. At the end of this time, it was opened and its contents were filtered. The recovered crystalline material was washed with copious quantities of $H_2O$ and was then dried at 165° C. in a forced air oven. The dried material was identified by X-ray diffraction as a crystalline material having the typical AMS-1B pattern with 100% crystallinity. Its X-ray diffraction pattern is reported in Table III above. The yield was approximately 2 grams.

EXAMPLE II

In this example, the AMS-1B crystalline borosilicate of Example I was used to produce a catalyst having isomerization capabilities.

The material from Example I was calcined at 1100° F. in air for 4 hours to remove the organic base. The calcined sieve was exchanged one time with a solution of 20 gm of $NH_4NO_3$ in 200 ml of $H_2O$ and then a second time with 20 gm of ammonium acetate in 200 ml of $H_2O$ at 190° F. for 2 hours. The exchanged borosilicate was dried and calcined in air by heating it to 900° F. for 4 hours, maintaining the borosilicate at 900° F. for 4 hours, and then cooling to 100° F. for 4 hours. The calcined material was exchanged with 100 ml of a 5% $Ni(NO_3)_2 \cdot 6H_2O$ solution for 2 hours at 190° F. The sieve was washed with $H_2O$ and the $Ni++$ was completely washed out of the sieve. The sieve was dried and calcined again using the above procedure. About 2 grams of the borosilicate were dispersed in 16.9 gm of $PHF-Al_2O_3$ (a gamma-alumina) hydrosol (8.9% solids) and mixed thoroughly. One milliliter of distilled $H_2O$ and 1 ml of concentrated $NH_4OH$ were mixed and added to the slurry with intensive mixing. The AMS-1B-$Al_2O_3$ mix was placed in a drying oven at 165° C. for 4 hours. The dried material was again calcined, using the above procedure. The calcined catalyst was crushed to 30–50-mesh material and impregnated with 2 ml of a solution of 5% $Ni(NO_3)_2 \cdot 6H_2O$ in distilled $H_2O$. The catalyst was again dried and activated by a fourth programmed calcination.

The calcined catalyst contained 65 weight percent borosilicate and 35 weight percent amorphous alumina with approximately 0.5 weight percent of the total solid as nickel. This material was analyzed by X-ray diffraction and the results are reported in Table I above. The amorphous alumina did not significantly alter the diffraction pattern generated.

One gram of the sized and activated catalyst was placed in the microreactor and sulfided with $H_2S$ for 20 minutes at room temperature. The catalyst was then placed under $H_2$ pressure and heated to 600° F. After 1 hour, feed was passed through the microreactor under the following once-through conditions:

Temperature: 800° F.
Pressure: 150 psig
WHSV: 6.28 hrs.$^{-1}$
H/HC, mole ratio: 7

The liquid feed and effluent streams for this operation are shown below. Because of the equipment limitations on the screening unit, only analyses on liquid streams were performed and reported. The light-end production over this catalyst was low from the gas chromatographic analysis made on the off-gas stream from the unit. The volume of off-gas was determined to not substantially reduce overall liquid yields over the catalyst.

| Component | Liquid Feed, wt.% | Liquid Product, wt.% |
|---|---|---|
| Paraffins and naphthenes | .03 | .08 |
| Benzene | — | 1.51 |
| Toluene | .077 | .26 |
| Ethylbenzene | 19.71 | 17.35 |
| para-Xylene | — | 19.43 |
| meta-Xylene | 79.80 | 46.40 |
| ortho-Xylene | .38 | 14.96 |
| $C_9+$* | — | 1.* |

*Approximate values only

EXAMPLE III

A solution of 600 gm $H_2O$, 2.5 gm $H_3BO_3$, and 7.5 gm of NaOH was prepared. 94.3 gm of tetra-n-propylammonium bromide was added to the original mixture and dissolved. Then 114.5 gm of Ludox AS-30 (30 wt.% solids) were added to the original liquid mixture with vigorous stirring.

The resulting mixture was placed in a reaction vessel and sealed. The bomb was placed in an oven at 165° C. for 7 days.

After washing and drying of the recovered solids as described in Example I, an X-ray diffraction analysis of this material was performed. The crystalline borosilicate was identified as AMS-1B with an X-ray diffraction pattern as described in Table III.

EXAMPLE IV

A borosilicate similar to that prepared in Example I was calcined at about 1100° F. (about 594° C.) and then analyzed to determine its overall composition. The results are shown below.

| Component | | |
|---|---|---|
| $SiO_2$, wt.% | | 94.90 |
| $B_2O_3$ | | 1.06 |
| $Na_2O$ | | 0.97 |
| $Al_2O_3$ | | 0.057 |
| $Fe_2O_3$ | | 0.029 |
| Volatiles* | | 2.984 |
| | Total | 100.000 |
| Mole Ratios | | |
| $SiO_2/B_2O_3$ | | 104.5 |
| $Na_2O/B_2O_3$ | | 1.0 |
| $SiO_2/Al_2O_3$ | | 2820 |
| $SiO_2/Fe_2O_3$ | | 8790 |
| $SiO_2/(Al_2O_3 + Fe_2O_3)$ | | 2150 |

*Assumed value to total 100%.

Other borosilicates were produced as generally described in Example I, except that the $H_3BO_3$ content was varied resulting in SiO₃/B₂O₃ molar ratios varying from 50 to 160, or higher, before the borosilicate was calcined or exchanged. After exchange with suitable catalytic materials the SiO$_2$/B$_2$O$_3$ molar ratio generally increased to a value of 80–100 for an as-prepared borosilicate which had a SiO$_2$/B$_2$O$_3$ molar ratio of around 50.

EXAMPLE V

Three borosilicate materials were prepared similar to the method described in Example I. The recovered materials were calcined at about 1000° F. (538° C.) and then analyzed for boron and silicon as reported below.

| Borosilicate | Wt. % Boron | Molar Ratio SiO$_2$/B$_2$O$_3$ |
|---|---|---|
| A | 0.66 | 47.4 |
| B | 0.64 | 49.1 |
| C | 0.71 | 44.5 |

After ion exchange with ammonium acetate the borosilicate was calcined at about 1000° F. (about 538° C.). The following was then determined:

| Borosilicate | Molar Ratio SiO$_2$/B$_2$O$_3$ |
|---|---|
| A | 75.1 |
| B | 71.2 |
| C | 64.2 |

Powder X-ray diffraction analysis was performed on samples of the above borosilicates after they had been calcined at 1000° F. but prior to ion exchange. The reported patterns are shown in Tables X, XI, and XII hereinbelow for relative intensities (I/I$_o$) of 10 or greater. Table VII hereinabove shows the interplanar spacings indicated from a strip chart for two runs of borosilicate A after 1000° F. (535° C.) calcination but before ion exchange.

TABLE X (Borosilicate A)

| Interplanar Spacing, d(Å) | Relative Intensity (I/I$_o$) |
|---|---|
| 11.34 | 38 |
| 10.13 | 30 |
| 6.01 | 14 |
| 4.35 | 11 |
| 4.26 | 14 |
| 3.84 | 100 |
| 3.72 | 52 |
| 3.65 | 31 |
| 3.44 | 14 |
| 3.33 | 16 |
| 3.04 | 16 |
| 2.97 | 22 |
| 2.48 | 11 |
| 1.99 | 20 |
| 1.66 | 12 |

TABLE XI (Borosilicate B)

| Interplanar Spacing, d(Å) | Relative Intensity (I/I$_o$) |
|---|---|
| 11.35 | 41 |
| 10.14 | 31 |
| 6.02 | 15 |
| 4.26 | 15 |

TABLE XI-continued (Borosilicate B)

| Interplanar Spacing, d(Å) | Relative Intensity (I/I$_o$) |
|---|---|
| 3.84 | 100 |
| 3.72 | 52 |
| 3.65 | 33 |
| 3.44 | 13 |
| 3.32 | 15 |
| 3.04 | 16 |
| 2.97 | 22 |
| 2.48 | 11 |
| 1.99 | 20 |
| 1.66 | 12 |

TABLE XII (Borosilicate C)

| Interplanar Spacing, d(Å) | Relative Intensity (I/I$_o$) |
|---|---|
| 11.40 | 33 |
| 10.17 | 29 |
| 6.03 | 13 |
| 5.62 | 10 |
| 4.27 | 14 |
| 3.84 | 100 |
| 3.73 | 51 |
| 3.65 | 30 |
| 3.44 | 13 |
| 3.32 | 16 |
| 3.05 | 16 |
| 2.98 | 21 |
| 1.99 | 19 |
| 1.66 | 12 |

EXAMPLE VI

A crystalline borosilicate was prepared by dissolving 0.8 gm of H$_3$BO$_3$ and 4.0 gm of NaOH in 200 gm of distilled H$_2$O. Then 31.2 gms of tetraethylammonium bromide (TEABr) were added and again dissolved. Finally, 29.0 gm of Ludox HS-40 (40 wt.% SiO$_2$, a silica sol stabilized with sodium and produced by DuPont) were added with vigorous stirring. The addition of the Ludox silica sol gave a curdy, gelatinous, milky solution. This reaction composition was placed in a reaction bomb, sealed, and designated reaction mixture A. The bomb was placed in a 165° C. oven and left there for 7 days. At the end of this time, it was opened and its contents were filtered. The recovered crystalline material was washed with copious quantities of H$_2$O and was then dried at 165° C. in a forced air oven and calcined. The calcined material was identified by X-ray powder diffraction analysis as a crystalline material having an X-ray diffraction pattern as reported in Table IX above. The yield was approximately 10.6 grams of solids.

Two other reactions mixtures were prepared similar to mixture A above except that 1.6 gm (reaction mixture B) and 3.2 gm (reaction mixture C) of H$_3$BO$_3$, respectively, were used in the formulations. The solids recovered from mixture B amounted to 8.8 gm and from mixture C amounted to 11.3 gm. The X-ray diffraction patterns for these products were similar to the pattern as reported in Table IX above.

The mole ratios of initial reactants for reaction mixtures A, B, and C are described in the Table below:

TABLE XIII

| Component | Mole Ratios | | |
| | Mixture A | Mixture B | Mixture C |
|---|---|---|---|
| OH$^-$/SiO$_2$ | 0.52 | 0.52 | 0.52 |

TABLE XIII-continued

| Component | Mole Ratios | | |
|---|---|---|---|
| | Mixture A | Mixture B | Mixture C |
| $SiO_2/B_2O_3$ | 29.97 | 14.93 | 7.46 |
| $Na_2O/(Na_2O + R_2O)$ | 0.52 | 0.52 | 0.52 |
| $H_2O/OH$ | 120.78 | 120.78 | 120.78 |

EXAMPLE VII

Ten grams of the crystalline borosilicate produced from mixture C in Example VI were exchanged five times for 1.5 hours for each exchange at about 90° C. with a single solution of 15 grams ammonium acetate in 150 ml of $H_2O$. The exchanged sieve was dried at 165° C. and then calcined in air for four hours at about 482° C.

Two grams of the above borosilicate were then impregnated with 2 grams of an aqueous solution of 5 wt.% nickel nitrate. The sieve was dried with agitation and then calcined in air for four hours at about 482° C.

The impregnated material was dispersed in alumina by mixing two grams of the borosilicate in 11.1 grams of PHF-alumina hydrosol (8.7 wt.% solids) and stirred for one hour. Then ammonium hydroxide was added to the mixture causing it to set-up. This slurry was then dried at 165° C. and thereafter calcined at about 482° C. for four hours. The dried product was crushed and sized to 30–50 mesh particle size and then calcined again for four hours at about 482° C.

One gram of the 30–50 mesh borosilicate material was placed in a small screening reactor and sulfided by contacting it with $H_2S$ gas at room temperature. The sulfided catalyst was heat treated at 314° C. for one hour in hydrogen at 150 psig.

Then a feed was passed on a once-through operation over the catalyst at 150 psi, 425° C., a molar ratio of hydrogen to hydrocarbon of 6.5 and a space velocity (WHSV) of 5.9. After about 138 hours on stream the feed and liquid effluents were analyzed as shown below:

| Component | Feed, Wt.% | Liquid Effluent, wt.% |
|---|---|---|
| Paraffins & Naphthenes | 0.05 | 0.07 |
| Benzene | — | 2.26 |
| Toluene | 0.07 | 0.56 |
| Ethylbenzene | 19.56 | 16.35 |
| para-Xylene | 8.65 | 18.63 |
| meta-Xylene | 47.83 | 41.27 |
| ortho-Xylene | 23.66 | 18.75 |
| $C_9$ + hydrocarbons | 0.22 | 2.11 |

The liquid feed and effluent analyses are shown above. Because of equipment limitations on the screening unit, only the liquid analysis is shown, the light-end production over the catalyst was low from the gas chromatographic analysis made on the off-gas stream from the unit. The volume of off-gas produced was determined to not substantially reduce the overall liquid yield. The catalyst was effective in producing paraxylene from other aromatics in the feed stream.

EXAMPLE VIII

Crystalline borosilicates produced generally as described in Example VI were identified by X-ray powder diffraction analysis. The X-ray diffraction pattern generated by this material is reproduced below for two different runs. In the second run, the reported peak intensity at 2.001 Angstroms was thought to be due in part to the alloy present in the sample holder and not totally produced by the borosilicate analyzed.

TABLE XIV

| Relative Intensity ($I/I_o$) | Interplanar Spacings, d(Å) | Two-Theta |
|---|---|---|
| 3 | 13.930 | 6.34 |
| 3 | 13.504 | 6.54 |
| 4 | 12.587 | 7.01 |
| 45 | 11.193 | 7.89 |
| 34 | 10.041 | 8.80 |
| 3 | 9.408 | 9.39 |
| 3 | 9.154 | 9.65 |
| 3 | 8.987 | 9.83 |
| 2 | 8.732 | 10.12 |
| 3 | 8.662 | 10.20 |
| 2 | 8.534 | 10.35 |
| 2 | 8.476 | 10.42 |
| 2 | 8.319 | 10.62 |
| 2 | 8.212 | 10.76 |
| 2 | 8.126 | 10.87 |
| 2 | 7.766 | 11.38 |
| 2 | 7.689 | 11.49 |
| 3 | 7.533 | 11.73 |
| 3 | 7.400 | 11.94 |
| 3 | 7.112 | 12.43 |
| 3 | 6.992 | 12.64 |
| 7 | 6.703 | 13.19 |
| 12 | 6.367 | 13.89 |
| 16 | 5.985 | 14.78 |
| 10 | 5.696 | 15.54 |
| 13 | 5.556 | 15.90 |
| 5 | 5.380 | 16.46 |
| 4 | 5.271 | 16.80 |
| 4 | 5.119 | 17.30 |
| 10 | 4.992 | 17.74 |
| 4 | 4.867 | 18.21 |
| 3 | 4.757 | 18.63 |
| 2 | 4.712 | 18.81 |
| 8 | 4.599 | 19.28 |
| 4 | 4.486 | 19.77 |
| 12 | 4.349 | 20.40 |
| 17 | 4.252 | 20.86 |
| 12 | 4.098 | 21.66 |
| 11 | 4.002 | 22.19 |
| 100 | 3.383 | 23.15 |
| 51 | 3.712 | 23.94 |
| 32 | 3.636 | 24.45 |
| 10 | 3.466 | 25.67 |
| 13 | 3.433 | 25.92 |
| 9 | 3.370 | 26.42 |
| 13 | 3.334 | 26.70 |
| 15 | 3.304 | 26.95 |
| 8 | 3.241 | 27.49 |
| 6 | 3.157 | 28.24 |
| 7 | 3.126 | 28.52 |

TABLE XV

| Relative Intensity ($I/I_o$) | Interplanar Spacings d(Å) | Two-Theta |
|---|---|---|
| 48 | 11.187 | 7.78 |
| 34 | 10.039 | 8.80 |
| 12 | 6.366 | 13.89 |
| 14 | 5.987 | 14.78 |
| 11 | 5.708 | 15.50 |
| 14 | 5.569 | 15.90 |
| 12 | 4.351 | 20.39 |
| 16 | 4.255 | 20.85 |
| 13 | 4.096 | 21.67 |
| 10 | 3.997 | 22.22 |
| 100 | 3.836 | 23.16 |
| 46 | 3.712 | 23.95 |
| 30 | 3.637 | 24.45 |
| 23 | 3.538 | 25.14 |
| 15 | 3.429 | 25.95 |
| 12 | 3.337 | 26.68 |
| 15 | 3.304 | 26.96 |
| 16 | 3.040 | 29.35 |
| 19 | 2.976 | 29.99 |

TABLE XV-continued

| Relative Intensity (I/I₀) | Interplanar Spacings d(Å) | Two-Theta |
|---|---|---|
| 13 | 2.479 | 36.19 |
| 13 | 2.031 | 44.56 |
| 18 | 2.001 | 45.27 |
| 21 | 1.986 | 45.62 |
| 10 | 1.865 | 48.78 |
| 11 | 1.658 | 55.34 |

EXAMPLE IX

Borosilicate A, which was discussed in Example V hereinabove, was submitted for additional X-ray diffraction analyses. The results are presented in Tables XVI, XVII, and XVIII hereinbelow.

TABLE XVI

X-ray Diffraction Data by Method No. 1 for Borosilicate A After Calcination at 1000° F.

| d(Å) | Assigned Strength | d(Å) | Assigned Strength |
|---|---|---|---|
| 11.08 | VS | 3.23 | VW |
| 9.96 | MS | 3.15 | VW |
| 7.39 | VW | 3.12 | VW |
| 6.66 | VW | 3.03 | VW |
| 6.32 | W | 2.96 | W |
| 5.95 | M | 2.84 | VW |
| 5.66 | W | 2.77 | VW |
| 5.54 | W | 2.72 | VW |
| 5.33 | VW | 2.59 | VW |
| 4.97 | VW | 2.49 | VW |
| 4.58 | VW | 2.47 | VW |
| 4.33 | VW | 2.38 | VW |
| 4.23 | W | 2.34 | VW |
| 3.98 | VW | 2.03 | VW |
| 3.82 | VS | 1.99 | VW |
| 3.70 | MS | 1.98 | VW |
| 3.62 | M | 1.94 | VW |
| 3.42 | VW | 1.90 | VW |
| 3.30 | W | 1.86 | VW |

TABLE XVII

X-ray Diffraction Data by Method No. 2 for Borosilicate A After Calcination at 1000° F.

| d(Å) | Assigned Strength | d(Å) | Assigned Strength |
|---|---|---|---|
| 11.07 | MS | 3.23 | VW |
| 9.94 | MS | 3.03 | W |
| 7.38 | VW | 2.97 | W |
| 6.67 | VW | 2.84 | VW |
| 6.32 | W | 2.71 | VW |
| 5.94 | W | 2.59 | VW |
| 5.66 | VW | 2.50 | VW |
| 5.53 | W | 2.47 | VW |
| 5.33 | VW | 2.40 | VW |
| 4.97 | VW | 2.38 | VW |
| 4.58 | VW | 2.31 | VW |
| 4.33 | VW | 2.06 | VW |
| 4.23 | W | 2.00 | W |
| 3.82 | VS | 1.98 | W |
| 3.69 | MS | 1.94 | VW |
| 3.62 | M | 1.90 | VW |
| 3.42 | W | 1.86 | VW |
| 3.29 | W | | |

TABLE XVIII

X-Ray Diffraction Data by Method No. 1 For Borosilicate A After Calcination at 1100° F.

| d(Å) | Assigned Strength | d(Å) | Assigned Strength |
|---|---|---|---|
| 11.09 | VS | 3.30 | W |
| 9.98 | MS | 3.23 | VW |
| 7.41 | VW | 3.12 | VW |
| 6.67 | VW | 3.03 | VW |
| 6.33 | W | 2.96 | W |
| 5.96 | M | 2.85 | VW |
| 5.67 | W | 2.72 | VW |
| 5.54 | W | 2.59 | VW |
| 5.34 | VW | 2.47 | VW |
| 4.98 | VW | 2.38 | VW |
| 4.58 | VW | 2.03 | VW |
| 4.33 | VW | 2.00 | VW |
| 4.24 | W | 1.98 | VW |
| 3.82 | VS | 1.94 | VW |
| 3.70 | MS | 1.90 | VW |
| 3.62 | M | 1.86 | VW |

EXAMPLE X

Powder X-ray diffraction analyses according to both Method No. 1 and Method No. 2 described hereinabove were performed on a sample of Borosilicate B, which was discussed in Example V hereinabove. The X-ray diffraction data obtained by Method No. 1 are presented in Table XIX hereinbelow and the X-ray diffraction data obtained by Method No. 2 are presented in Table XX hereinbelow.

TABLE XIX

X-Ray Diffraction Data by Method No. 1 for Borosilicate B After Calcination at 1000° F.

| d(Å) | Assigned Strength | d(Å) | Assigned Strength |
|---|---|---|---|
| 11.09 | VS | 3.23 | VW |
| 9.98 | MS | 3.15 | VW |
| 7.40 | VW | 3.12 | VW |
| 6.67 | VW | 3.03 | W |
| 6.33 | W | 2.97 | W |
| 5.96 | M | 2.93 | VW |
| 5.67 | W | 2.85 | VW |
| 5.54 | W | 2.77 | VW |
| 5.34 | VW | 2.72 | VW |
| 5.10 | VW | 2.59 | VW |
| 4.98 | VW | 2.50 | VW |
| 4.59 | VW | 2.47 | VW |
| 4.34 | VW | 2.40 | VW |
| 4.24 | W | 2.38 | VW |
| 4.05 | VW | 2.34 | VW |
| 3.98 | VW | 2.03 | VW |
| 3.83 | VS | 2.00 | VW |
| 3.70 | MS | 2.00 | VW |
| 3.63 | M | 1.98 | VW |
| 3.46 | VW | 1.94 | VW |
| 3.42 | VW | 1.90 | VW |
| 3.32 | VW | | |
| 3.29 | W | 1.86 | VW |

TABLE XX

X-ray Diffraction Data by Method No. 2 for Borosilicate B After Calcination at 1000° F.

| d(Å) | Assigned Strength | d(Å) | Assigned Strength |
|---|---|---|---|
| 11.09 | MS | 3.16 | VW |
| 9.97 | M | 3.12 | VW |
| 7.39 | VW | 3.03 | W |
| 6.67 | VW | 2.97 | W |
| 6.33 | W | 2.93 | VW |
| 5.96 | W | 2.85 | VW |
| 5.68 | W | 2.77 | VW |
| 5.55 | W | 2.72 | VW |
| 5.33 | VW | 2.67 | VW |
| 5.10 | VW | 2.64 | VW |
| 4.98 | VW | 2.59 | VW |

TABLE XX-continued

X-ray Diffraction Data by Method No. 2 for
Borosilicate B After Calcination at 1000° F.

| d(Å) | Assigned Strength | d(Å) | Assigned Strength |
|---|---|---|---|
| 4.59 | VW | 2.50 | VW |
| 4.34 | VW | 2.47 | VW |
| 4.24 | W | 2.40 | VW |
| 4.06 | VW | 2.38 | VW |
| 3.98 | VW | 2.31 | VW |
| 3.83 | VS | 2.10 | VW |
| 3.70 | MS | 2.06 | VW |
| 3.63 | M | 2.00 | W |
| 3.46 | VW | 1.98 | W |
| 3.42 | W | 1.94 | VW |
| 3.33 | W | 1.90 | VW |
| 3.29 | W | 1.86 | VW |
| 3.23 | VW | | |

EXAMPLE XI

Another AMS-1B crystalline borosilicate, hereinafter identified as Borosilicate D, was prepared.

Powder X-ray diffraction analyses according to both Method No. 1 and Method No. 2 described hereinabove, were performed on a sample of Borosilicate D. The X-ray diffraction data obtained by Method No. 1 are presented in Table XXI hereinbelow and the X-ray diffraction data obtained by Method No. 2 are presented in Table XXII hereinbelow.

TABLE XXI

X-ray Diffraction Data by Method No. 1 for
Borosilicate D After Calcination at 1000° F.

| d(Å) | Assigned Strength | d(Å) | Assigned Strength |
|---|---|---|---|
| 11.09 | VS | 3.29 | W |
| 9.95 | MS | 3.23 | VW |
| 7.41 | VW | 3.15 | VW |
| 6.66 | VW | 3.12 | VW |
| 6.32 | W | 3.03 | W |
| 5.95 | M | 2.96 | W |
| 5.67 | W | 2.85 | VW |
| 5.54 | W | 2.76 | VW |
| 5.34 | VW | 2.71 | VW |
| 4.98 | VW | 2.59 | VW |
| 4.58 | VW | 2.47 | VW |
| 4.33 | VW | 2.38 | VW |
| 4.23 | W | 2.00 | VW |
| 3.82 | VS | 1.98 | VW |
| 3.70 | MS | 1.94 | VW |
| 3.62 | M | 1.90 | VW |
| 3.42 | VW | 1.86 | VW |

TABLE XXII

X-ray Diffraction Data by Method No. 2 for
Borosilicate D After Calcination at 1000° F.

| d(Å) | Assigned Strength | d(Å) | Assigned Strength |
|---|---|---|---|
| 11.15 | MS | 3.43 | VW |
| 10.01 | M | 3.30 | W |
| 7.42 | VW | 3.24 | VW |
| 6.70 | VW | 3.04 | W |
| 6.35 | VW | 2.97 | W |
| 5.98 | W | 2.72 | VW |
| 5.68 | VW | 2.50 | VW |
| 5.56 | W | 2.48 | VW |
| 5.35 | VW | 2.39 | VW |
| 4.99 | VW | 2.32 | VW |
| 4.60 | VW | 2.07 | VW |
| 4.35 | VW | 2.00 | W |
| 4.25 | W | 1.99 | W |
| 3.84 | VS | 1.94 | VW |
| 3.71 | MS | 1.91 | VW |
| 3.63 | M | 1.86 | VW |

EXAMPLE XII

Some of the characteristic X-ray diffraction interplanar spacings and their corresponding assigned strengths for the borosilicates presented hereinabove are compiled in Table XXIII hereinbelow.

TABLE XXIII

| BOROSILICATE | I | | III | | V | | VI | | VII | | IX | | A X | |
|---|---|---|---|---|---|---|---|---|---|---|---|---|---|---|
| TABLE | 1 | | 1 | | 2 | | 2 | | 2 | | 1 | | 2 | |
| METHOD | 1100° F. | | 165° C. | | 1000° F. | | 165° C. | | 1000° F. | | 1000° F. | | 1000° F. | |
| TREAT | d(Å) | A.S.* | d(Å) | A.S. | d(Å) | A.S. | d(Å) | A.S. | d(Å) | d(Å) | d(Å) | A.S. | d(Å) | A.S. |
| | 11.04 | VS | 11.04 | S | 11.3 | M | 11.4 | W | 11.3 | 11.2 | 11.04 | MS | 11.34 | M |
| | 10.04 | MS | 9.82 | S | 10.1 | M | 10.1 | W | 10.2 | 10.0 | 10.04 | M | 10.13 | M |
| | 5.98 | M | 5.90 | W | 6.01 | W | | | 6.02 | 5.98 | 5.98 | W | 6.01 | W |
| | 3.83 | VS | 3.80 | VS | 3.84 | VS | 3.84 | VS | 3.85 | 3.85 | 3.83 | VS | 3.84 | VS |
| | 3.72 | MS | 3.67 | S | 3.72 | MS | 3.73 | MS | 3.72 | 3.70 | 3.72 | MS | 3.72 | MS |
| | 3.64 | M | 3.60 | MS | 3.65 | M | 3.66 | M | 3.64 | 3.64 | 3.64 | M | 3.65 | M |
| | 2.98 | W | 2.96 | W | 2.97 | M | 2.98 | W | 2.96 | 2.97 | 2.98 | W | 2.97 | M |
| | 1.99 | W | 1.99 | W | 1.99 | M | 1.99 | W | 1.99 | | 1.99 | M | 1.99 | M |

| BOROSILICATE | B | | C | | XIV | | XV | | A XVI | | A XVII | | B XX | |
|---|---|---|---|---|---|---|---|---|---|---|---|---|---|---|
| TABLE | XI | | XII | | | | | | | | | | | |
| METHOD | 2 | | 2 | | 1 | | 1 | | 1 | | 2 | | 2 | |
| TREAT | 1000° F. | | 1000° F. | | 165° C. | | 165° C. | | 1000° F. | | 1000° F. | | 1000° d(Å) | |
| | d(Å) | A.S. | d(Å) | A.S. | d(Å) | A.S. | d(Å) | A.S. | d(Å) | A.S. | d(Å) | A.S. | d(Å) | A.S. |
| | 11.35 | MS | 11.40 | M | 11.19 | MS | 11.19 | MS | 11.08 | VS | 11.07 | MS | 11.09 | MS |
| | 10.14 | M | 10.17 | M | 10.04 | M | 10.04 | M | 9.96 | MS | 9.94 | MS | 9.97 | M |
| | 6.02 | W | 6.03 | W | 5.99 | W | 5.99 | W | 5.95 | M | 5.94 | W | 5.96 | W |
| | 3.84 | VS | 3.84 | VS | 3.84 | VS | 3.84 | VS | 3.82 | VS | 3.82 | VS | 3.83 | VS |
| | 3.72 | MS | 3.73 | MS | 3.71 | MS | 3.71 | MS | 3.70 | MS | 3.69 | MS | 3.70 | MS |
| | 3.65 | M | 3.65 | M | 3.64 | M | 3.64 | M | 3.62 | M | 3.62 | M | 3.63 | M |
| | 2.97 | M | 2.98 | M | | | 2.98 | W | 2.96 | W | 2.97 | W | 2.97 | W |
| | 1.99 | M | 1.99 | W | | | 1.99 | M | 1.99 | VW | 1.98–2.00 | W | 1.98–2.00 | W |

| BOROSILICATE | B | D | D | A |
|---|---|---|---|---|
| TABLE | XIX | XXI | XXII | XVIII |
| METHOD | 1 | 1 | 2 | 1 |

TABLE XXIII-continued

| TREAT | 1000° F. | | 1000° F. | | 1000° F. | | 1000° F. | |
|---|---|---|---|---|---|---|---|---|
| | d(Å) | A.S. | d(Å) | A.S. | d(Å) | A.S. | d(Å) | A.S. |
| | 11.09 | VS | 11.09 | VS | 11.15 | MS | 11.09 | VS |
| | 9.98 | MS | 9.95 | MS | 10.01 | M | 9.98 | MS |
| | 5.96 | M | 5.95 | M | 5.98 | W | 5.96 | M |
| | 3.83 | VS | 3.82 | VS | 3.84 | VS | 3.82 | VS |
| | 3.70 | MS | 3.70 | MS | 3.71 | MS | 3.70 | MS |
| | 3.63 | M | 3.62 | M | 3.63 | M | 3.62 | M |
| | 2.97 | W | 2.96 | W | 2.97 | W | 2.96 | W |
| | 1.98–2.00 | VW | 1.98–2.00 | VW | 1.99–2.00 | W | 1.99–2.00 | VW |

*A.S. = assigned strength

The data in Table XXIII are summarized in Table XXIV in ranges of values.

TABLE XXIV

| | X-ray Diffraction Data Summary | | |
|---|---|---|---|
| Interplanar | Assigned Strengths After Treatment | | |
| Spacings | at 1000° F. | at 1000° F. | at 165° C. |
| 11.04–11.40 | M - MS | MS - VS | W - MS |
| 9.82–10.20 | M - MS | M - MS | W - MS |
| 5.90–6.03 | W - M | W - M | W |
| 3.80–3.85 | VS | VS | VS |
| 3.67–3.73 | MS | MS | MS |
| 3.60–3.65 | M | M | M - MS |
| 2.96–2.98 | W - M | W | W |
| 1.98–2.00 | VW - M | W - M | W - M |

In view of the values presented in Table XXIV, the X-ray diffraction patterns of crystalline AMS-1B borosilicates can be represented in general terms by the information shown in Table XXV hereinbelow.

TABLE XXV

| X-ray Diffraction Pattern of AMS-1B Borosilicates | | |
|---|---|---|
| Interplanar | Assigned Strengths For | |
| Spacings | All | Calcined at 1000° F.–1100° F. |
| 11.2 ± 0.2 | W - VS | M - VS |
| 10.0 ± 0.2 | W - MS | M - MS |
| 5.97 ± 0.07 | W - M | W - M |
| 3.82 ± 0.05 | VS | VS |
| 3.70 ± 0.05 | MS | MS |
| 3.62 ± 0.05 | M - MS | MS |
| 2.97 ± 0.02 | W - M | W - M |
| 1.99 ± 0.02 | VW - M | VW - M |

Therefore, in broad terms, the X-ray diffraction patterns of crystalline AMS-1B borosilicates comprise the interplanar spacings shown in Table XXV and the assigned strengths shown therein depending upon the presence or absence of calcination of the material prior to X-ray diffraction analysis.

EXAMPLE XIII

As mentioned hereinabove, the alkylammonium cations can be furnished by various compounds. To demonstrate this, 5 borosilicates were prepared by employing tetraethylammonium bromide, tetrabutylammonium bromide, or 1,6-hexane diamine as the source or precursor of the alkylammonium cations. Reactants were used in the amounts listed in Table XXVI hereinbelow. The mixtures of reactants were crystallized at 165° C. for 7 days. The resulting solid material was removed by filtration and washed with distilled water. The solid material was dried at 165° C. and then calcined at about 1000° F. (about 538° C.) for 4 hours. In all 5 of these preparations, the solid materials were identified by X-ray diffraction as AMS-1B borosilicates.

TABLE XXVI

| | Preparation Information | | | | |
|---|---|---|---|---|---|
| Borosilicate | E | F | G | H | I |
| H₂O, gm | 200 | 200 | 200 | 600 | 600 |
| NaOH, gm | 4.0 | 4.0 | 4.0 | 5.0 | 6.0 |
| H₃BO₃, gm | 0.8 | 1.6 | 3.2 | 5.0 | 10.0 |
| Precursor* Type | TEAB | TEAB | TEAB | TBAB | 1,6-HD |
| wt., gm. | 31.2 | 31.2 | 31.2 | 100.0 | 100.0 |
| Ludox Type | HS-40 | HS-40 | HS-40 | HS-40 | HS-40 |
| Wt., gm | 29.0 | 29.0 | 29.0 | 76.0 | 77.5 |
| Boron, wt.% | — | — | — | 0.39 | 0.62 |

*Precursor of alkylammonium cations
TEAB tetraethylammonium bromide
TBAB tetrabutylammonium bromide
1,6-HD 1,6-hexane diamine

What is claimed is:

1. A crystalline borosilicate which comprises a molecular sieve material having the following composition in terms of mole ratios of oxides:

$$0.9 \pm 0.2 M_{2/n}O:B_2O_3:YSiO_2:ZH_2O$$

wherein M is at least one cation having a valence of n, Y is between 4 and about 600, and Z is between 0 and about 160, and providing an X-ray diffraction pattern comprising the following X-ray diffraction lines and assigned strengths:

| d (Å) | Assigned Strength |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M |

2. The borosilicate of claim 1, wherein, after said borosilicate has been calcined at a temperature of about 1000° F. to about 1100° F., said calcined borosilicate provides an X-ray diffraction pattern comprising the following X-ray diffraction lines and assigned strengths:

| d(Å) | Assigned Strength |
|---|---|
| 11.2 ± 0.2 | M - VS |
| 10.0 ± 0.2 | M - MS |
| 5.97 ± 0.07 | W - M |
| 3.82 ± 0.05 | VS |
| 3.70 ± 0.05 | MS |
| 3.62 ± 0.05 | M |
| 2.97 ± 0.02 | W - M |

| d(Å) | Assigned Strength |
|---|---|
| 1.99 ± 0.02 | VW - M |

3. The borosilicate of claim 1, wherein Z is between 0 and about 40.

4. The borosilicate of claim 1, wherein Y is between 4 and about 500.

5. The borosilicate of claim 1, wherein M comprises a member selected from the group consisting of alkylammonium cation, ammonium cation, hydrogen cation, a metal cation, and mixtures thereof.

6. The borosilicate of claim 1, wherein M is a nickel cation.

7. The borosilicate of claim 2, wherein Y is between 4 and about 500.

8. The borosilicate of claim 4, wherein Y is between about 4 and about 300.

9. The borosilicate of claim 7, wherein Y is between about 4 and about 300.

10. The borosilicate of claim 8, wherein Y is between about 40 and about 160.

11. The borosilicate of claim 9, wherein Y is between about 40 and about 160.

12. The borosilicate of claim 10, wherein Z is between 0 and about 40.

13. The borosilicate of claim 11, wherein Z is between 0 and about 40.

14. A method for preparing a crystalline borosilicate which comprises a molecular sieve material providing an X-ray diffraction pattern comprising the following X-ray diffraction lines and assigned strengths:

| d(Å) | Assigned Strength |
|---|---|
| 11.2 ± 0.2 | W - VS |
| 10.0 ± 0.2 | W - MS |
| 5.97 ± 0.07 | W - M |
| 3.82 ± 0.05 | VS |
| 3.70 ± 0.05 | MS |
| 3.62 ± 0.05 | M - MS |
| 2.97 ± 0.02 | W - M |
| 1.99 ± 0.02 | VW - M | and having the following composition in terms of mole ratios of oxides:

$$0.9 \pm 0.2 M_{2/n}O : B_2O_3 : Y SiO_2 : Z H_2O$$

wherein M is at least one cation having a valence of n, Y is between 4 and about 600, and Z is between 0 and about 160, which method comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

15. The method of claim 14, wherein said reaction time is about 1 hour to about 4 weeks.

16. The method of claim 14, wherein said reaction temperature is about 90° C. to about 250° C.

17. The method of claim 14, wherein said mixture prepared during said method of preparation has the ratios of the initial reactant concentrations in the following ranges:

$OH^-/SiO_2$: 0.01–11
$R_2O/(R_2O + M_{2/n}O)$: 0.2–0.97
$H_2O/OH^-$: 10–4000
$SiO_2/B_2O_3$: 5–400 wherein R is an alkylammonium cation, M is an alkali metal or alkaline earth metal, and n is the valence of M.

18. The method of claim 17, wherein said reaction time is about 1 hour to about 4 weeks.

19. The method of claim 18, wherein said reaction temperature is about 90° C. to about 250° C.

20. The method of claim 18, wherein said reaction time is about 6 hours to about 1 week.

21. A crystalline borosilicate having a composition in terms of mole ratios of oxides as follows:

$$0.9 \pm 0.2 M_{2/n}O : B_2O_3 : Y SiO_2 : Z H_2O$$

wherein M is at least one cation having a valence of n, Y is between 4 and about 500, and Z is between 0 and about 160, said borosilicate showing the X-ray diffraction lines of Table V of the specification.

22. A crystalline borosilicate having a composition in terms of mole ratios of oxides as follows:

$$0.9 \pm 0.2 M_{2/n}O : B_2O_3 : Y SiO_2 : Z H_2O$$

wherein M is at least one cation having a valence of n, Y is between 4 and about 500, and Z is between 0 and about 160, said borosilicate showing the X-ray diffraction lines and assigned strengths substantially as described in Table V of the specification.

23. The composition of claim 22 further characterized in that Y is a value in the range of from about 4 to about 200.

24. The composition of claim 22 further characterized in that M is a member selected from the group consisting of alkylammonium, ammonium, hydrogen, metal cations, and mixtures thereof.

25. The composition of claim 22 further characterized in that M comprises hydrogen, nickel, and an alkali metal.

26. The composition of claim 22 further characterized in that Z is in the range of from 0 to about 40.

27. The composition of claim 22 further characterized in that Y is in the range of from about 50 to about 160.

28. A crystalline borosilicate having a composition in terms of oxides as follows:

$$0.9 \pm 0.2 [W R_2O + (1-W) ] M_{2/n}O : B_2O_3 : Y SiO_2 : Z H_2O$$

wherein R is tetrapropylammonium cation, M is an alkali metal cation, W is greater than 0 and less than or equal to 1, Y is between 4 and about 500, Z is between 0 and about 160, said borosilicate showing the X-ray diffraction lines and assigned strengths substantially as described in Table VI of the specification.

29. The crystalline borosilicate formed by calcining the crystalline borosilicate of claim 28 at a temperature in the range of from about 500° F. to about 1500° F.

30. A crystalline borosilicate having a composition in terms of mole ratios of oxides as follows:

$$0.9 \pm 0.2 M_{2/n}O : B_2O_3 : Y SiO_2 : Z H_2O$$

wherein M is at least one cation having a valence of n, Y is between 4 and about 300, and Z is between 0 and about 160, said borosilicate having the X-ray diffraction lines and assigned strengths substantially as described in Table II of the specification.

31. The composition of claim 30 further characterized in that M is selected from the group consisting of alkylammonium, ammonium, hydrogen, metal cations, or mixtures thereof.

32. The composition of claim 31 further characterized in that M comprises nickel.

33. The composition of claim 30 further characterized in that M comprises hydrogen, nickel, and an alkali metal.

34. The composition of claim 30 further characterized in that Z is in the range of from 0 to about 40.

35. The composition of claim 34 further characterized in that Y is in the range of from about 50 to about 160.

36. The composition of claim 30 further characterized in that said borosilicate has X-ray diffraction lines and assigned strengths substantially as described in Table I of the specification.

37. The composition of claim 36 further characterized in that Y is between about 4 and about 200 and Z is between 0 and about 40.

38. A crystalline borosilicate having a composition in terms of oxides as follows:

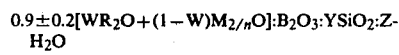

$0.9 \pm 0.2[WR_2O+(1-W)M_{2/n}O]:B_2O_3:YSiO_2:ZH_2O$ wherein R is a tetrapropylammonium cation, M is an alkali metal cation, W is greater than 0 and less than or equal to 1, Y is between about 4 and about 300, Z is between 0 and about 160, said borosilicate having the X-ray diffraction lines and assigned strengths substantially as described in Table IV of the specification.

39. The crystalline borosilicate formed by calcining the crystalline borosilicate of claim 38 at a temperature in the range of about 500° F. to about 1600° F.

40. A method for preparing a crystalline borosilicate possessing X-ray diffraction lines and assigned strengths substantially as shown in Table III, which method comprises preparing a mixture containing an oxide of silicon, an oxide of boron, a base of an alkali or alkaline earth metal, a tetraethylammonium cation, and water; maintaining said mixture at reaction conditions including a temperature in the range of from about 100° C. to about 250° C. to effect formation of said crystalline borosilicate.

41. The method of claim 40 further characterized in that said mixture is further characterized in terms of mole ratios of oxides in the following ranges:

$OH^-/SiO_2$: 0.06–11
$SiO_2/B_2O_3$: 5–300
$R_2O/R_2O+M_{2/n}O$): 0.2–0.97 wherein M is the alkali or alkaline earth metal, n is the valence of M, and R is a tetraethylammonium cation.

* * * * *

UNITED STATES PATENT OFFICE
CERTIFICATE OF CORRECTION

Patent No. 4,269,813      Dated May 26, 1981

Inventor(s) MARVIN R. KLOTZ

It is certified that error appears in the above-identified patent and that said Letters Patent are hereby corrected as shown below:

Column 1, line 8, "of applications" should be -- of co-pending applications --.

Column 2, line 5, "are reacted" should be -- is reacted --.

Column 4, line 47, "Xray" should be -- X-ray --.

Column 6, line 67, "Strengths" should be -- Strength --.

Column 12, line 68, "tetrahydra" should be -- tetrahedra --.

Column 13, line 2, "that single" should be -- that a single --.

Column 13, line 17, "$SiO_2$-$B_2O_3$" should be -- $SiO_2/B_2O_3$ --.

Column 15, lines 13-14, "(tetraalkylammonium)" should be -- (tetraethylammonium) --.

Column 15, line 48, "acontaining" should be -- a mixture containing --.

Column 15, line 67, "comprising a the" should be -- comprising the --.

Column 16, line 62, "are as" should be -- as --.

Column 17, line 63, "$OH^-/SiO_2$: 0.01-11" should be -- $OH^-/SiO_2$      0.01-11 --.

Column 17, line 64, "$R_2O/(R_2O+M_{2/n}O)$: 0.2-0.97" should be -- $R_2O/(R_2O+M_{2/n}O)$      0.2-0.97 --.

Column 17, line 65, "$H_2O/OH^-$: 10-4000" should be -- $H_2O/OH^-$      10-4000 --.

Column 17, line 66, "$SiO_2/B_2O_3$: 5-400" should be -- $SiO_2/B_2O_3$      5-400 --.

UNITED STATES PATENT OFFICE
CERTIFICATE OF CORRECTION

Patent No. 4,269,813  Dated May 26, 1981

Inventor(s) MARVIN R. KLOTZ

It is certified that error appears in the above-identified patent and that said Letters Patent are hereby corrected as shown below:

Column 18, line 9, "comprise" should be -- comprises --.

Column 19, line 59, "amorophous" should be -- amorphous --.

Column 20, line 3, "Temperature: 800°F." should be -- Temperature    800°F. --.

Column 20, line 4, "Pressure: 150 psig" should be -- Pressure    150 psig --.

Column 20, line 5, "WHSV: 6.28 hrs.$^{-1}$" should be -- WHSV    6.28 hrs.$^{-1}$ --.

Column 20, line 6, "H/HC, mole ratio: 7" should be -- H/HC, mole ratio    7 --.

Column 20, line 64, "$Fe_2O_3$" should be -- $Fe_2O_3$) --.

Column 22, line 54, "reactions" should be -- reaction --.

Column 24, line 28, "5.556" should be -- 5.566 --.

Column 28, line 58, "1000° d(Å)" should be -- 1000°F. --.

Column 29, line 21, "at 1000°F.    at 1000°F." should be
         -- at 1000°F.          at 1100°F. --.

Column 32, line 3, "$OH^-/SiO_2$: 0.01-11" should be -- $OH^-/SiO_2$    0.01-11 --.

Column 32, line 4, "$R_2O/(R_2O+M_{2/n}O)$: 0.2-0.97" should be
         -- $R_2O/(R_2O+M_{2/n}O)$    0.2-0.97 --.

Column 32, line 5, "$H_2O/OH^-$: 10-4000" should be -- $H_2O/OH^-$    10-4000 --.

UNITED STATES PATENT OFFICE
CERTIFICATE OF CORRECTION

Patent No. 4,269,813      Dated May 26, 1981

Inventor(s) MARVIN R. KLOTZ

It is certified that error appears in the above-identified patent and that said Letters Patent are hereby corrected as shown below:

Column 32, line 6, "$SiO_2/B_2O_3$: 5-400" should be -- $SiO_2/B_2O_3$    5-400 --.

Column 34, line 24, "$OH^-/SiO_2$: 0.06-11" should be -- $OH^-/SiO_2$    0.06-11 --.

Column 34, line 25, "$SiO_2/B_2O_3$: 5-300" should be -- $SiO_2/B_2O_3$    5-300 --.

Column 34, line 26, "$R_2O/R_2O+M_{2/n}O$): 0.2-0.97" should be -- $R_2O/(R_2O+M_{2/n}O)$    0.2-0.97 --.

Signed and Sealed this

Eleventh Day of September 1984

[SEAL]

Attest:

GERALD J. MOSSINGHOFF

Attesting Officer     Commissioner of Patents and Trademarks